United States Patent [19]

Skuballa et al.

[11] Patent Number: 5,079,259
[45] Date of Patent: Jan. 7, 1992

[54] PHARMACEUTICALLY ACTIVE 9-CHLOROPROSTAGLANDINS

[75] Inventors: Werner Skuballa; Bernd Raduechel; Helmut Vorbrueggen; Walter Elger; Olaf Loge; Ekkehard Schillinger, all of Berlin, Fed. Rep. of Germany

[73] Assignee: Schering Aktiengesellschaft, Berlin and Bergkamen, Fed. Rep. of Germany

[21] Appl. No.: 96,232

[22] Filed: Sep. 8, 1987

Related U.S. Application Data

[60] Continuation of Ser. No. 754,702, Jul. 15, 1985, abandoned, which is a continuation of Ser. No. 581,741, Feb. 16, 1984, abandoned, which is a division of Ser. No. 387,140, Jun. 10, 1982, Pat. No. 4,444,788, which is a continuation-in-part of Ser. No. 215,762, Dec. 10, 1980, abandoned.

[30] Foreign Application Priority Data

Dec. 10, 1979 [DE] Fed. Rep. of Germany ....... 2950027

[51] Int. Cl.[5] .................... C07C 177/00; A61K 31/557
[52] U.S. Cl. .................................... 514/530; 514/573; 549/415; 549/472; 556/441; 560/121; 562/503
[58] Field of Search .............. 560/121; 562/503; 514/530, 573; 549/472, 415; 556/441

[56] References Cited

U.S. PATENT DOCUMENTS 4,346,228  8/1982  Skuballa .............................. 560/53

OTHER PUBLICATIONS

Arroniz, Prostaglanding, 16, 47, 1978.

Primary Examiner—Robert Gerstl
Attorney, Agent, or Firm—Millen, White & Zelano

[57] ABSTRACT

A 9-chloroprostane of the formula

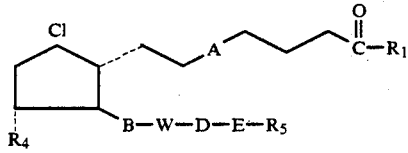

wherein the 9-chlorine atom can be in the $\alpha$ or $\beta$-position and $R_1$, $R_4$, $R_5$, A, B, W, D and E are as described hereinafter which are useful as medical agents.

13 Claims, No Drawings

PHARMACEUTICALLY ACTIVE 9-CHLOROPROSTAGLANDINS

CROSS REFERENCE TO RELATED APPLICATIONS

This application is a continuation of application Ser. No. 754,702, filed July 15, 1985, now abandoned, which is a continuation of Ser. No. 581,741 of Feb. 16, 1984, now abandoned, which is a division of Ser. No. 387,140 of Jun. 10, 1982, now U.S. Pat. No. 4,444,788, which is a continuation-in-part of Ser. No. 215,762, of Dec. 10, 1980, now abandoned.

BACKGROUND OF THE INVENTION

The present invention relates to novel 9-chloroprostaglandin derivatives, a process for their preparation and their use as medicinal agents.

From the very voluminous state of the art of prostaglandins and their analogs, they are well known to be suitable for the treatment of mammals, including man, because of their biological and pharmacological properties. Their use as medicinal agents, however, frequently encounters difficulties. Most of the natural prostaglandins possess a period of effectiveness too brief for therapeutic purposes, since they are too quickly metabolically degraded by various enzymatic processes. All of the attempted structural alterations in these molecules usually have as a goal increasing their duration of activity as well as their selectivity of effectiveness.

SUMMARY OF THE INVENTION

It is accordingly an object of this invention to provide novel 9-chloroprostaglandin derivatives exhibiting an excellent specificity of effectiveness, an improved activity, a longer duration of activity than natural prostaglandins, and a suitability especially for oral administration.

Upon further study of the specification and appended claims, further objects and advantages of this invention will become apparent to those skilled in the art.

These objects have been attained by this invention by providing 9-chloroprostane derivatives of Formula I

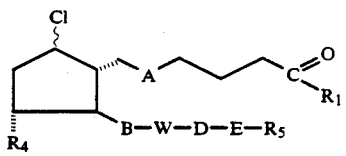

wherein the 9-chlorine atom can be in the $\alpha$- or $\beta$-position, $R_1$ is $OR_2$ wherein $R_2$ is hydrogen, alkyl, cycloalkyl, a heterocyclic residue; or is $NHR_3$ wherein $R_3$ is an acid residue or hydrogen;

A is $-CH_2-CH_2-$ or cis$-CH=CH-$;

B is $-CH_2-CH_2-$, trans$-CH=CH-$, or $-C\equiv C-$;

W is free or functionally modified hydroxymethylene or a free or functionally modified

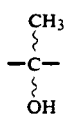

group, wherein the OH-group can be in the $\alpha$- or $\beta$-position D and E together are a direct bond; or D is straight-chain or branched-chain alkylene of 1-10 carbon atoms, optionally substituted by fluorine, and E is oxygen, sulfur or a direct bond;

$R_4$ is free or functionally modified hydroxy;

$R_5$ is a hydrocarbon aliphatic group, optionally substituted by halogen; cycloalkyl; optionally substituted aryl; or a heterocyclic group;

and, when $R_1$ is hydroxy, the physiologically compatible salts thereof with bases.

DETAILED DISCUSSION

Suitable alkyl groups $R_2$ include straight chain or branched alkyl of 1-10 carbon atoms, such as, for example, methyl, ethyl, propyl, butyl, isobutyl, tert-butyl, pentyl, neopentyl, heptyl, hexyl, decyl, etc. The alkyl groups $R_2$ can optionally be mono- to polysubstituted (e.g., by 2-4 substituents) by halogen, $C_{1-4}$-alkoxy, optionally substituted aryl or aroyl, each of 6-10 C atoms, di-$C_{1-4}$-alkylamine, or tri-$C_{1-4}$-alkylammonium. Single substitution is preferred. Examples of substituents include fluorine, chlorine, bromine, phenyl, dimethylamino, diethylamino, methoxy, ethoxy, etc. Preferred alkyl groups $R_2$ are those of 1-4 carbon atoms, such as, for example, methyl, ethyl, propyl, dimethylaminopropyl, isobutyl, butyl, etc. Suitable substituents for the substituted aryl or aroyl substituents include those mentioned below as substituents for the $R_2$ aryl groups.

Aryl groups $R_2$ can be substituted or unsubstituted and generally are of 6-10 C atoms, e.g., phenyl, 1-naphthyl, or 2-naphthyl. These can be substituted by 1-3 halogen atoms (e.g., F, Cl, Br), a phenyl group, 1-3 alkyl groups of 1-4 carbon atoms each, a chloromethyl, fluoromethyl, trifluoromethyl, carboxy, hydroxy, or alkoxy group of 1-4 carbon atoms. Substitutents on the 3- and 4-positions of the phenyl ring are preferred, for example, by fluorine, chlorine, alkoxy, or trifluoromethyl, or in the 4-position by hydroxy.

Suitable cycloalkyl groups $R_2$ can contain 4-10, preferably 5 or 6 carbon atoms in the ring. The rings can be substituted by alkyl groups of 1-4 carbon atoms, e.g., by 1-3 such alkyl groups. Examples include cyclopentyl, cyclohexyl, methylcyclohexyl, adamantyl, etc.

Suitable heterocyclic groups $R_2$ include 5- or 6-membered heterocycles, preferably aromatic, containing at least 1 hetero atom, e.g., 1-2 such atoms, preferably nitrogen, oxygen or sulfur. Examples of such equivalent heterocycles are 2-furyl, 2-thienyl, 2-pyridyl, 3-pyridyl, 4-pyridyl, oxazolyl, thiazolyl, pyrimidinyl, pyridazinyl, pyrazinyl, and others.

The acid residue $R_3$ is any of the many known physiologically compatible acid residues. Preferred acids are organic, hydrocarbon carboxylic acids and sulfonic acids of 1-15 carbon atoms of the aliphatic, cycloaliphatic, aromatic, aromatic-aliphatic, etc. series. Since this acid residue is not critical, many equivalents exist and may be utilized as well, e.g., those of the heterocyclic series. These acids can be saturated, unsaturated and/or polybasic and/or substituted in conventional manner. Examples of substituents include alkyl, hydroxy, alkoxy, oxo, amino, halogen, etc. The following carboxylic acids can be cited by way of example: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid, benzoic acids substituted by halogen, trifluoromethyl, hydroxy, alkoxy or carboxy groups, nicotinic acid, isonicotinic acid, furan-2-carboxylic acid, cyclopentylpropionic acid, etc. Particularly preferred acyl groups are those of up to 10 carbon atoms. Examples of suitable sulfonic acids include methanesulfonic acid, ethanesulfonic acid, isopropylsulfonic acid, β-chloroethanesulfonic acid, butanesulfonic acid, cyclopentanesulfonic acid, cyclohexanesulfonic acid, benzenesulfonic acid, p-toluenesulfonic acid, p-chlorobenzenesulfonic acid, N,N-dimethylaminosulfonic acid, N,N-diethylaminosulfonic acid, N,N-bis(β-chloroethyl)-aminosulfonic acid, N,N-diisobutylaminosulfonic acid, N,N-dibutylaminosulfonic acid, pyrrolidinopiperidino-, piperazino-, N-methylpiperazino-, and morpholinosulfonic acids.

The hydroxy groups in W and $R_4$ can be functionally modified, for example, by etherification or esterification, wherein the free or modified hydroxy group in W can be in the α- or β-position.

Suitable ether and acyl residues are fully conventional and well known to persons skilled in the art. In general these conventional protective groups include, e.g., those disclosed in Mc. Omie. Ed., Protective Groups in Organic Chemistry, Plenum Press, N.Y., 1973, whose disclosure is incorporated by reference herein. Among these many equivalents, preferred are ether residues which can be readily split off, such as, for example, tetrahydropyranyl, tetrahydrofuranyl, α-ethoxyethyl, trimethylsilyl, dimethyl-tert-butylsilyl, and tribenzylsilyl. Suitable acyl residues are those recited in connection with $R_3$ above; especially worth mentioning, for example, are acetyl propionyl, butyryl, and benzoyl.

Suitable hydrocarbon aliphatic groups $R_5$ include straight-chain or branched, saturated or unsaturated such residues, preferably saturated residues, of 1-10, especially 1-6 carbon atoms, which can optionally be substituted by optionally substituted aryl, e.g., the $R_2$ aryl groups defined above, substituted and unsubstituted, and by halogen as also defined above for $R_2$ alkyl substitution. Examples include methyl, ethyl, propyl, butyl, isobutyl, tert-butyl, pentyl, hexyl, heptyl, octyl, butenyl, isobutenyl, propenyl, pentenyl, benzyl, m-chlorobenzyl, and p-chlorobenzyl groups.

Suitable $R_5$ cycloalkyl, substituted or unsubstituted aryl and heterocyclic groups are in accordance with the foregoing discussion of the corresponding $R_2$ groups.

The alkylene group D can be straight chain or branched, saturated or unsaturated. It can be an alkylene of 1-10, especially 1-5 carbon atoms, which can be optionally substitute by 1-3 fluorine atoms. Saturated residues are preferred. Examples include methylene, fluoromethylenedifluoromethylene, ethylene, 1,2-propylene, ethylethylene, trimethylene, tetramethylene, pentamethylene, 1,1-difluoroethylene, 1-fluoroethylene, 1-methyltetramethylene, 1-methyltrimethylene, 1-methylene-ethylene, 1-methylenetetramethylene, etc.

B preferably is trans—CH=CH—.

$R_5$ and/or D/E can also be preferably chosen so that the lower chain contains an additional double bond, preferably at the 18-position (PG nomenclature). They can also independently be preferably chosen so that the 16-position is substituted by one or two alkyl groups, e.g., methyl or ethyl, preferably methyl, and/or the 19-position is substituted by alkyl, e.g., methyl or ethyl, preferably methyl.

Inorganic and organic bases are suitable for the salt formation, and are known to those skilled in the art for the preparation of physiologically compatible salts. Examples include alkali metal hydroxides, such as sodium and potassium hydroxide, alkaline earth hydroxides, such as calcium hydroxide, ammonia, amines, such as ethanolamine, diethanolamine, triethanolamine, N-methylglucamine, morpholine, tris(hydroxymethyl)methylamine, etc.

The present invention furthermore relates to a process for the preparation of the 9-chloroprostane derivatives of Formula I of this invention, wherein, conventionally, a compound of Formula II

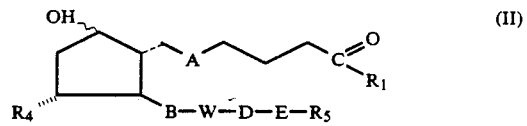

wherein
the OH-group can be in the α- or β-position,
$R_1$, B, D, E, and $R_5$ are as defined above, and
free OH-groups in $R_4$ and W, as defined above, are blocked, (a) is reacted via an intermediate sulfonic acid ester, with a chloride of Formula III, $R_6Cl$, wherein $R_6$ is lithium, sodium, potassium, or tetraalkylammonium wherein each alkyl is of 1-6 carbon atoms, or (b) is chlorinated using a carbon tetrachloride/triphenylphosphine reagent, and, optionally, in the reaction products obtained in reactions (a) or (b), in any desired sequence, blocked hydroxy groups are liberated, and/or free hydroxy groups are esterified, and/or double bonds are hydrogenated, and/or an etherified and/or esterified carboxy group ($R_1$=$OR_2$) is saponified, and/or a free carboxy group ($R_1$=OH) is esterified, and/or a free carboxy group ($R_1$=OH) is converted into an amide ($R_1$=$NHR_3$)

The conversion of the compounds of Formula II into 9-sulfonic acid esters takes place conventionally using an alkylsulfonyl chloride or arylsulfonyl chloride in the presence of an amine, e.g., pyridine or triethylamine, at temperatures of −60° to +100° C., preferably −20° to +50° C. The nucleophilic substitution of the 9-sulfonate by a chlorine atom takes place using an alkali metal chloride, preferably lithium chloride or tetraalkylammonium chloride, tetrabutylammonium chloride being preferred, in an inert solvent, such as, for example, dimethylformamide, dimethylacetamide, dimethyl sulfoxide, dimethoxyethane, tetrahydrofuran, etc., at temperatures of 0° to 100° C., preferably 20° to 80° C.

The compounds of Formula II are converted to the compounds of Formula I with carbon tetrachloride and triphenylphosphine in an inert solvent, such as, for example, dimethylformamide, dimethylacetamide, acetonitrile, methylene chloride, etc. at temperatures of 0° to 80° C., preferably 20° to 45° C.

Functionally modified hydroxy groups are liberated by following conventional methods. For example, hydroxy blocking groups, e.g., tetrahydropyranyl, can be split off in an aqueous solution of an organic acid, e.g., oxalic acid, acetic acid, propionic acid, and others, or in an aqueous solution of an inorganic acid, e.g., hydrochloric acid. To improve solubility, a water-miscible inert organic solvent is suitably added. Examples of suitable organic solvents are alcohols, such as methanol and ethanol, and ethers, such as dimethoxyethane, dioxane, and tetrahydrofurau. Tetrahydrofuran is preferably employed. The splitting-off step is preferably conducted at temperatures of 20° to 80° C.

The acyl groups can be saponified, for example, with alkali metal or alkaline earth carbonates or hydroxides in an alcohol or in an aqueous solution of an alcohol. Suitable alcohols are aliphatic alcohols, such as, for example, methanol, ethanol, butanol, etc., preferably methanol. Examples of alkali metal carbonates and hydroxides are the potassium and sodium salts. The potassium salts are preferred. Suitable examples of alkaline earth carbonates and hydroxides are calcium carbonate, calcium hydroxide, and barium carbonate. The reaction takes place at −10° to +70° C., preferably at about +25° C.

The introduction of the ester group $OR_2$ as $R_1$, wherein $R_2$ is an alkyl group of 1-10 carbon atoms, takes place according to methods known to those skilled in the art. The 1-carboxy compounds can be reacted, for example, by mixing a solution of the diazohydrocarbon in an inert solvent, preferably in diethyl ether, with the 1-carboxy compound in the same solvent or in another inert solvent, e.g., methylene chloride. After the reaction is completed (usually 1-30 minutes), the solvent is removed, and the ester is purified in the usual way. Diazoalkanes are either known or can be prepared according to conventional methods [Org. Reactions 8:389-394 (1954)].

The ester group $—OR_2$ wherein $R_2$ is a substituted or unsubstituted aryl group (including heterocycles) is introduced as $R_1$ in accordance with methods known to persons skilled in the art. For example, the 1-carboxy compounds can be reacted with the corresponding aryl-hydroxy compounds with dicyclohexylcarbodiimide in the presence of a suitable base, e.g., pyridine or triethylamine, in an inert solvent. Solvents include methylene chloride, ethylene chloride, chloroform, ethyl acetate, tetrahydrofuran, preferably chloroform. The reaction is conducted at temperatures of −30° to +50° C., preferably at about 10° C.

If C≡C-double bonds present in the primary product are to be reduced, the hydrogenation is accomplished according to methods known per se.

The hydrogenation of the 5,6-double bond takes place conventionally at low temperatures, preferably at about −20° C., in a hydrogen atmosphere in the presence of a noble metal catalyst. A suitable catalyst is, for example, 10% palladium on carbon.

If the 5,6- as well as the 13,14-double bonds are hydrogenated, the reaction is carried out at a higher temperature, preferably at about 20° C.

The prostaglandin derivatives of Formula I wherein $R_1$ is hydroxy can be converted, using suitable amounts of the corresponding inorganic bases, into a salt, via neutralization. For example, when dissolving the corresponding PG acids in water containing the stoichiometric quantity of the base, the solid, inorganic salt is obtained after removal of the water by evaporation or after adding a water-miscible solvent, e.g., alcohol or acetone.

To produce an amine salt, which is effected in the usual way, the PG acid is dissolved, for example, in a suitable solvent, e.g., ethanol, acetone, diethyl ether, acetonitrile, or benzene, and at least the stoichiometric amount of the amine is added to this solution. In this way, the salt is ordinarily obtained in the solid phase, or it is isolated in the usual manner after evaporation of the solvent.

The amide group $NHR_3$ as $R_1$ is also introduced according to methods known to those skilled in the art. The carboxylic acids of Formula I ($R_1$=OH) are first converted into the mixed anhydride in the presence of a tertiary amine, such as, for example, triethylamine, with the use of the isobutyl ester of chloroformic acid. The reaction of the mixed anhydride with the alkali metal salt of the corresponding amide or with ammonia ($R_3$=H) takes place in an inert solvent or solvent mixture, e.g., tetrahydrofuran, dimethoxyethane, dimethylformamide, hexamethylphosphoric triamide, at temperatures of −30° to +60° C., preferably at 0° to 30° C.

Another method for introducing the amide group $NHR_3$ as $R_1$ resides in reacting a 1-carboxylic acid of Formula I ($R_1$=OH) wherein free hydroxy groups are optionally blocked intermediarily, with compounds of Formula IV

$$O=C=N—R_3 \qquad (IV)$$

wherein $R_3$ is as defined above.

The reaction of the compound of Formula I ($R_1$=OH) with an isocyanate of Formula IV takes place optionally with the addition of a tertiary amine, e.g., triethylamine or pyridine. The reaction can be conducted without a solvent or in an inert solvent, preferably acetonitrile, tetrahydrofuran, acetone, dimethylacetamide, methylene chloride, diethyl ether, toluene, at temperatures of −80° to 100° C., preferably at 0° to 30° C.

If the starting compound contains OH-groups in the prostane residue, then these OH-groups are also reacted. If, end products are desired which contain free hydroxy groups in the prostane residue, then starting compounds are advantageously utilized wherein these groups are blocked intermediarily by preferably readily cleavable ether or acyl residues.

All the compounds of formula II are known or are routinely preparable using well known, fully conventional methods, e.g., as described in J. S. Binderer and R. Binderer, prostaglandin synthesis, Academic Press, N.Y., 1977, and in A. Mitra, The synthesis of prostaglandins, Wiley-Interscience, N.Y., 1977 whose disclosures are incorporated by reference herein.

As compared with PGE derivatives, the novel 9-chloroprostaglandins are distinguished by greater stability.

The novel 9-chloroprostane derivatives of general Formula I are valuable pharmaceuticals, since they exhibit, with a similar spectrum of activity, a substantially improved higher specificity and, above all, substantially improved effectiveness than the corresponding natural prostaglandins.

The novel prostaglandin analogs of this invention have a strong luteolytic effect, i.e., trigger luteolysis; moreover, significantly lower doses are required than for the corresponding natural prostaglandins.

Also, for triggering abortions, especially upon oral administration, substantially lesser quantities of these novel prostaglandin analogs are necessary, as compared with the natural prostaglandins.

Via conventional pharmaceutical protocols, e.g., when recording the isotonic uterus contraction in narcotized rats and on the isolated rat uterus, it can be seen that the compounds of this invention are substantially more active, and their activities are of longer duration than for the natural prostaglandins.

The novel prostaglandin derivatives of this invention are also suitable, after a single enteral or parenteral administration, for inducing menstruation or interrupting pregnancy. They are further suitable for synchronizing the sexual cycle in female mammals, such as rabbits, cattle, horses, pigs, etc. Furthermore, the prostaglandin derivatives of this invention are suitable for use in preparations for diagnostic or therapeutic interventions, e.g., cervix dilation.

The high tissue specificity of the compounds of this invention having an antifertility effect is also demonstrated by standard protocols, e.g., studies on other smooth-muscle organs, such as, for example, on the guinea pig ileum or on the isolated rabbit trachea, where a substantially lower stimulation is found than in case of the natural prostaglandins. The compounds of this invention also have a bronchospasmolytic effect. Additionally, they reduce the swelling of the nasal mucous membrane.

The active agents of this invention inhibit gastric acid secretion, display a cytoprotective and ulcer-healing activity, and thus counteract the undesirable consequences of nonsteroidal antiinflammatory agents (prostaglandin synthesis inhibitors).

Several of the compounds exhibit a blood pressure lowering effect, a regulating activity in arrhythmia of the heart, and an inhibitory action on platelet aggregation, with the conventional usage possibilities resulting therefrom.

For medical use, the active agents can be converted into a form suitable for inhalation, or for oral, parenteral, or local (e.g., vaginal) administration, as is fully conventional.

Aerosol solutions can be suitably prepared for inhalation purposes.

Tablets, dragees, or capsules are suitable, for example, for oral administration.

For parenteral administration, sterile, injectable, aqueous or oily solutions are utilized.

For vaginal administration, suppositories are suitable and customary, for example.

Accordingly, the invention also concerns medicinal agents based on the compounds of Formula I and the customary excipients and vehicles for use in treating mammals, including humans.

Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxy-methylcellulose, polyvinyl pyrrolidone, etc. The pharmaceutical preparations can be sterilized and if desired, mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For enteral application, particularly suitable are tablets, dragees, suppositories or capsules having talc and/or carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

The active agents of this invention thus can be used in conjunction with the excipients known and conventional in galenic pharmacy, for example, for the production of preparations to trigger abortion, to control the menstrual cycle, to induce labor, or to treat hypertonia. For these purposes, but also for other applications mentioned above, the preparations can contain unit doses of 0.01–50 mg of the active compound. Daily doses are generally 0.1–50 mg/kg and administration can be analogous to the known agents $PGE_2$ and 16-phenoxy-prostaglandin-$E_2$-methanesulfonamide, e.g., as abortive agents or agents for cervix dilatation.

Dosages for a given host can be determined, e.g., by customary comparison of the activities of the subject compound and of a known agent by means of an appropriate, conventional pharmacological protocol.

The novel prostaglandin analogs of this invention are substantially more selective with regard to potency, as compared with known PG analogs in causing prostaglandin-like biological responses, and have a substantially longer duration of biological activity. Accordingly, each of these novel prostaglandin analogs is surprisingly and unexpectedly more useful than one of the corresponding conventional prostaglandins for at least one of the pharmacological purposes indicated above because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller doses of the novel prostaglandin analog are frequently effective in attaining the desired result.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(5Z,13E)-(9R,11R,15R)-9-Chloro-11,15-dihydroxy-16-phenoxy-17,18,19,20-tetranor-5,13-prostadienoic Acid Methyl Ester At 0° C., 3.8 g of p-toluenesulfonic acid chloride is added to a solution of 5.72 g of (5Z,13E)-(9S,11R,15R)-9-hydroxy-11,15-bis(tetrahydropyran-2-yloxy)-16-phenoxy-17,18,19,20-tetranor-5,13-prostadienoic acid methyl ester (prepared from the corresponding acid in methylene chloride with 0.5-molar ethereal diazomethane solution at 0° C.) in 17 ml of pyridine; the mixture is agitated for 16 hours at ice bath temperature and 48 hours at room temperature. Then the mixture is combined with 15 ml of water, stirred for 2.5 hours at room temperature, mixed with 1 liter of ether, shaken in succession with water, 5% sulfuric acid, 5% sodium bicarbonate solution, and water, then dried over magnesium sulfate and evaporated under vacuum, thus obtaining 6.56 g of the 9-tosylate as a colorless oil.

IR: 2950, 2875, 1733, 1600, 1590, 1496, 1365, 1240, 974 cm$^{-1}$.

A solution of 3.6 g of the 9-tosylate in 150 ml of dimethylformamide is agitated for 4 hours with 2.1 g of lithium chloride at 60° C. under argon. The mixture is subsequently poured on 10% sodium chloride solution, extracted three times with a mixture of ether/hexane 1+1, the organic extract is shaken three times with water, dried over magnesium sulfate, and evaporated under vacuum.

During this step, 2.9 g of the 9β-chloro compound is obtained as a colorless oil.

IR: 2955, 1734, 1603, 1591, 978 cm$^{-1}$.

To split off the tetrahydropyranyl ether, 2.9 g of the above-obtained crude product is stirred for 16 hours at room temperature with 80 ml of a mixture of acetic acid/water/tetrahydrofuran (65+35+10) and then evaporated under vacuum. The residue is purified by chromatography on silica gel. With ether as the eluent, 1.1 g of the title compound i obtained as a colorless oil.

EXAMPLE 2

IR: 3600, 3400 (broad), 2940, 1730, 1603, 1591, 975 cm$^{-1}$.

EXAMPLE 2

(5Z,13E)-(9R,11R,15R)-9-Chloro-11,15-dihydroxy-16-phenoxy-17,18,19,20-tetranor-5,13-prostadienoic Acid 450 mg of the methyl ester prepared according to Example 1 is stirred for 5 hours with 15 ml of a solution of potassium hydroxide in ethanol and water (preparation: 2 g of potassium hydroxide is dissolved in 75 ml of ethanol and 25 ml of water). The mixture is then acidified with 10% citric acid solution to pH 4, extracted three times with methylene chloride, the organic extract is washed once with brine, dried over magnesium sulfate, and evaporated under vacuum. Chromatography of the residue on silica gel with methylene chloride/methanol as the eluent yields 405 mg of the title compound as a colorless oil.

IR: 3600, 3400 (broad), 2930, 2855, 1710, 1600, 1590, 971 cm$^{-1}$.

EXAMPLE 3

(13E)-(9R,11R,15R)-9-Chloro-11,15-dihydroxy-16-phenoxy-17,18,19,20-tetranor-13-prostenoic Acid Methyl Ester At 0° C., 720 mg of p-toluenesulfonic acid chloride is added to a solution of 1.15 g of (13E)-(9S,11R,15R)-9-hydroxy-11,15-bis(tetrahydropyran-2-yloxy)-16-phenoxy-17,18,19,20-tetranor-13-prostenoic acid methyl ester (prepared from the corresponding acid in methylene chloride with 0.5-molar ethereal diazomethane solution at 0° C.) in 3.5 ml of pyridine; the mixture is stirred for 16 hours at 0° C. and for 48 hours at 25° C. Subsequently, the mixture is combined with 0.3 ml of water, agitated for 2,5 hours at 25° C., mixed with ether, shaken in succession with water, 5% sulfuric acid, 5% sodium bicarbonate solution, and water, and dried over magnesium sulfate, whereafter the mixture is evaporated under vacuum. Yield: 1.4 g of the 9-tosylate as a colorless oil.

IR: 2950, 2873, 1732, 1600, 1591, 1495, 1365, 1240, 975 cm$^{-1}$.

A solution of 0.92 g of the 9-tosylate in 60 ml of dimethylformamide is agitated for 4 hours with 550 mg of lithium chloride at 60° C. under argon. The mixture is then poured on 10% sodium chloride solution, extracted three times with a mixture of ether/hexane 1+1, the organic extract is shaken three times with water, dried over magnesium sulfate, and evaporated under vacuum, thus obtaining 0.72 g of the 9β-chloro compound as a colorless oil.

IR: 2955, 1733, 1602, 1590, 978 cm$^{-1}$.

To split off the tetrahydropyranyl ether, 0.72 g of the above-obtained crude product is agitated for 16 hours at 25° with 15 ml of a mixture of acetic acid/water/tetrahydrofuran (65+35+10) and then evaporated under vacuum. The residue is purified by chromatography on silica gel. With ether as the eluent, 0.29 g of the title compound is obtained as a colorless oil.

IR: 3600, 3400 (broad), 2945, 1731, 1602, 1590, 976 cm$^{-1}$.

EXAMPLE 4

(13E)-(9R,11R,15R)-9-Chloro-11,15-dihydroxy-16-phenoxy-17,18,19,20-tetranor-13-prostenoic Acid Analogously to Example 2, 0.25 g of the methyl ester produced by following Example 3 yields 0.19 g of the title compound as a colorless oil.

IR: 3600, 3420 (broad), 2935, 2857, 1710, 1600, 1592, 972 cm$^{-1}$.

EXAMPLE 5

(5Z,13E)-(9R,11R,15R)-9-Chloro-11,15-dihydroxy-16-(m-chlorophenoxy)-17,18,19,20-tetranor-5,13-prostadienoic Acid Methyl Ester A solution of 2.95 g of (5Z,13E)-(9S,11R,15R)-9-hydroxy-11,15-bis(tetrahydropyran-2-yloxy)-16-(m-chlorophenoxy)-17,18,19,20-tetranor-5,13-prostadienoic acid methyl ester (prepared from the corresponding acid in methylene chloride with 0.5-molar diazomethane solution at 0° C.) in 8 ml of pyridine is combined at 0° C. with 1.9 g of p-toluenesulfonic acid chloride; the mixture is stirred for 16 hours at ice bath temperature and 48 hours at room temperature. Subsequently the mixture is combined with 5 ml of water, agitated for 2.5 hours at room temperature, mixed with 0.4 l of ether, shaken in succession with water, 5% sulfuric acid, 5% sodium bicarbonate solution, and water, dried over magnesium sulfate, and evaporated under vacuum, thus obtaining 3.4 g of the 9-tosylate as a colorless oil.

IR: 2955, 2873, 1733, 1600, 1588, 972 cm$^{-1}$.

A solution of 3.4 g of the 9-tosylate in 150 ml of dimethylformamide is agitated for 4 hours with 2.0 g of lithium chloride at 60° C. under argon. The mixture is then poured on 10% sodium chloride solution, extracted three times with a mixture of ether/hexane 1+1, the organic extract is shaken three times with water, dried over magnesium sulfate, and evaporated under vacuum, thus obtaining as the crude product 2.7 g of the 9β-chloro compound in the form of a colorless oil IR: 2955, 1733, 1600, 1587, 975 cm$^{-1}$.

To split off the tetrahydropyranyl ether, 2.7 g of the above-obtained crude product is stirred for 16 hours at room temperature with 70 ml of a mixture of acetic acid/water/tetrahydrofuran (65+35+10) and then evaporated under vacuum. Purification of the residue on silica gel yields, with ether as the eluent, 0.95 g of the title compound as a colorless oil.

IR: 3600, 3420 (broad), 2940, 1732, 1600, 1588, 976 cm$^{-1}$.

EXAMPLE 6

(5Z,13E)-(9R,11R,15R)-9-Chloro-11,15-dihydroxy-16-(m-chlorophenoxy)-17,18,19,20-tetranor-5,13-prostadienoic Acid Analogously to Example 2, 510 mg of the methyl ester prepared according to Example 5 yields 460 mg of the title compound as a colorless oil.

IR: 3600, 3400 (broad), 2940, 2860, 1710, 1600, 1588, 973 cm$^{-1}$.

EXAMPLE 7

(13E)-(9R,11R,15R)-9-Chloro-11,15-dihydroxy-16-(m-chlorophenoxy) 17,18,19,20-tetranor-13-prostenoic Acid Methyl Ester A solution of 600 mg of (13E)-(9S,11R,15R)-9-hydroxy-11,15-bis(tetrahydropyran-2-yloxy)-16-(m-chlorophenoxy)-17,18,19,20-tetranor-13-prostenoic acid methyl ester (prepared by hydrogenating (5Z,13E)-(9S,11R,15R)-9-hydroxy-11,15-bis(tetrahydropyran-2-yloxy)-16-(m-chlorophenoxy)-17,18,19,20-tetranor-5,13-prostadienoic acid methyl ester in ethyl acetate at 20° C. in palladium 10% on carbon and one equivalent of hydrogen) in 2 ml of pyridine is combined at 0° C. with 390 mg of p-toluenesulfonic acid chloride, agitated for 16 hours at ice bath temperature and for 48 hours at room temperature, and then combined with 0.5 ml of water. The mixture is agitated for 3 hours at room temperature, diluted with ether, shaken in succession with water, 5% sulfuric acid, 5% sodium bicarbonate solution, and water, dried over magnesium sulfate, and evaporated under vacuum, thus obtaining 680 mg of the 9-tosylate as a colorless oil.

IR: 2955, 2873, 1732, 1600, 1588, 974 cm$^{-1}$.

A solution of 680 mg of the 9-tosylate in 15 ml of dimethylformamide is agitated for 4 hours with 220 mg of lithium chloride at 60° C. under argon. The mixture is then poured on 10% sodium bicarbonate solution, extracted three times with a mixture of ether/hexane 1+1, the organic extract is shaken three times with water, dried over magnesium sulfate, and evaporated under vacuum, thus obtaining as the crude produce 520 mg of the 9β-chloro compound in the form of an oil.

IR: 2955, 1732, 1600, 1588, 975 cm$^{-1}$.

To split off the tetrahydropyranyl ether, 520 mg of the above-obtained crude product is stirred for 16 hours at room temperature with 10 ml of a mixture of acetic acid/water/tetrahydrofuran (65+35+10) and then evaporated under vacuum. After purifying the residue on silica gel with ether as the eluent, 225 mg of the title compound is obtained as a colorless oil.

EXAMPLE 8

(13E)-(9R,11R,15R)-9-Chloro-11,15-dihydroxy-16-(m-chlorophenoxy)-17,18,19,20-tetranor-13-prostenoic Acid In analogy to Example 2, 200 mg of the methyl ester prepared according to Example 7 yields 165 mg of the title compound as a colorless oil.

IR: 3600, 3420 (broad), 2944, 2860, 1710, 1600, 1588, 975 cm$^{-1}$.

EXAMPLE 9

(5Z,13E)-(9R,11R,15R)-9-Chloro-11,15-dihydroxy-16,16-dimethyl-5,13-prostadienoic Acid Methyl Ester A solution of 1.3 g of (5Z,13E)-(9S,11R,15R)-16,16-dimethyl-9-hydroxy-11,15-bis(tetrahydropyran-2-yloxy)-5,13-prostadienoic acid methyl ester, 800 mg of triphenylphosphine and 370 mg of carbon tetrachloride in 6 ml of acetonitrile is agitated for 2 hours at 80° C. Thereafter the mixture is diluted with 40 ml of water, extracted three times with a mixture of ether/hexane (1+1), the organic extract is washed with water, dried over magnesium sulfate, and evaporated under vacuum. Chromatography of the evaporation residue on silica gel yields, with hexane/ether 4+1, 0.55 g of the 9β-chloro compound as a colorless oil.

IR: 2960, 1733, 976 cm$^{-1}$.

For tetrahydropyranyl ether cleavage, 0.5 g of the above-obtained 9β-chloro compound is agitated with 5 ml of a mixture of acetic acid /water/tetrahydrofuran (65+35+10) and then evaporated under vacuum. The residue is purified by chromatography on silica gel. With ether as the eluent, 0.35 g of the title compound is obtained as a colorless oil.

IR: 3600, 3400 (broad), 2945, 1732, 976 cm$^{-1}$.

EXAMPLE 10

(5Z,13E)-(9R,11R,15R)-9-Chloro-11,15-dihydroxy-16,16-dimethyl-5,13-prostadienoic Acid Analogously to Example 2, 0.3 g of the methyl ester prepared according to Example 9 yields 0.24 g of the title compound as a colorless oil.

IR: 3600, 3420 (broad), 2944, 1709, 975 cm$^{-1}$.

EXAMPLE 11

(5Z,13E)-(9R,11R,16RS)-9-Chloro-11,15α-dihydroxy-16-methyl-5,13-prostadienoic Acid Methyl Ester At 0° C., 760 mg of p-toluenesulfonic acid chloride is added to a solution of 1.1 g of (5Z,13E)-(9S,11R,16RS)-9-hydroxy-16-methyl-11,15α-bis(tetrahydropyran-2-yloxy)-5,13-prostadienoic acid methyl ester (produced from the corresponding acid in methylene chloride with 0.5-molar diazomethane solution at 0° C.) in 3.5 ml of pyridine; the mixture is agitated for 16 hours at 0° C. and for 48 hours at 25° C. After the mixture has been worked up as described in Example 1, 1.4 g of the 9-tosylate is obtained as a colorless oil.

IR: 2955, 2870, 1732, 975 cm$^{-1}$.

A solution of 1.4 g of the 9-tosylate in 60 ml of dimethylformamide is agitated for 4 hours with 840 mg of lithium chloride at 60° C. under argon. The usual working-up procedure yields 1.1 g of the 9β-chloro compound as an oil.

IR: 2960, 1732, 975 cm$^{-1}$.

To split off the tetrahydropyranyl ether, 1.1 g of the above-obtained crude product is stirred for 16 hours at room temperature with 35 ml of a mixture of acetic acid/water/tetrahydrofuran (65+35+10) and then evaporated under vacuum. After chromatography of the residue on silica gel, using ether as the eluent, 0.6 g of the title compound is obtained as an oil.

IR: 3600, 3420 (broad), 2950, 1733, 976 cm$^{-1}$.

EXAMPLE 12

(5Z,13E)-(9R,11R,16RS)-9-Chloro-11,15o-dihydroxy-16-methyl-5,13-prostadienoic Acid Analogously to Example 2, 0.5 g of the methyl ester produced according to Example 11 yields 0.39 g of the title compound as a colorless oil.

IR: 3600, 3400 (broad), 2945, 1710, 976 cm$^{-1}$.

EXAMPLE 13

(5Z,13E)-(9R,11R,15S)-9-Chloro-11,15-dihydroxy-15-methyl-5,13-prostadienoic Acid Methyl Ester At 0° C., 691 mg of p-toluenesulfonic acid chloride is added to a solution of 1 g of (5Z,13E)-(9S,11R,15S)-9-hydroxy-15-methyl-11,15-bis(tetrahydropyran-2-yloxy)-5,13-prostadienoic acid methyl ester (prepared from the corresponding acid in methylene chloride with 0.5-molar diazomethane solution) in 3.5 ml of pyridine; the mixture is stirred for 16 hours at 0° C., then for 48 hours at 25° C. After the mixture has been worked up according to Example 1, 1.25 g of the 9-tosylate is obtained as a colorless oil.

IR: 2950, 270, 1735, 1601, 1365, 1175, 978, 905 cm$^{-1}$.

A solution of 1.20 g of the 9-tosylate in 50 ml of dimethylformamide is agitated for 4.5 hours with 720 mg of lithium chloride at 60° C. under argon. The mixture is worked up according to Example 1, thus obtaining 900 mg of the 9β-chloro compound as an oil.

IR: 2955, 2868, 1735, 978 cm$^{-1}$.

To split off the blocking groups, 800 mg of the thus-obtained 9β-chloro compound is stirred with 20 ml of a mixture of acetic acid/water/tetrahydrofuran (65+35+10) for 20 hours at 25° C. Evaporation under vacuum and chromatography of the residue on silica gel with methylene chloride yield 400 mg of the title compound as an oil.

IR: 3600, 3420 (broad), 2955, 2870, 1735, 976 cm$^{-1}$.

EXAMPLE 14

(5Z,13E)-(9R,11R,15S)-9-Chloro-11,15-dihydroxy-15-methyl-5,13-prostadienoic Acid In analogy to Example 2, 300 mg of the methyl ester prepared according to Example 13 yields 230 mg of the title compound as an oil.

IR: 3600, 3400, 2950, 1710, 978 cm$^{-1}$.

EXAMPLE 15

(5Z,13E)-(9R,11R,15R,16RS)-9-Chloro-11,15-dihydroxy-16-fluoro-5,13-prostadienoic Acid Methyl Ester A mixture of 1.2 g of (5Z,13E)-(9S,11R,15R,16RS)-9-hydroxy-16-fluoro-11,15-bis(tetrahydropyran-2-yloxy)-5,13-prostadienoic acid methyl ester (prepared from the corresponding acid in methylene chloride with 0.5-molar diazomethane solution at 0° C.), 800 mg of p-toluenesulfonic acid chloride, and 4 ml of pyridine is agitated for 16 hours at 0° C., then for 48 hours at 25° C. The mixture is worked up according to Example 1. Yield: 1.45 g of the 9-tosylate as an oil.

IR: 2952, 2870, 1732, 1601, 1360, 1170, 978, 906 cm$^{-1}$.

1.25 g of the thus-obtained tosylate is heated with 725 mg of lithium chloride in 50 ml of dimethylformamide under agitation for 4 hours to 60° C. After the mixture has been worked up according to Example 1, 925 mg of the 9β-chloro compound is obtained as an oil.

IR: 2950, 1735, 976 cm$^{-1}$.

To split off the blocking groups, 900 mg of the thus-produced 9β-chloro compound is stirred with 25 ml of a mixture of glacial acetic acid/water/tetrahydrofuran (65+35+10) for 20 hours at 25° C. Evaporation under vacuum and chromatography of the residue on silica gel with methylene chloride yield 450 mg of the title compound as an oil.

IR: 3605, 3420, 2952., 2868, 1735, 978 cm$^{-1}$.

EXAMPLE 16

(5Z,13E)-(9R,11R,15R,16RS)-9-Chloro-11,15-dihydroxy-16-fluoro-5,13-prostadienoic Acid Analogously to Example 2, 400 mg of the methyl ester produced according to Example 15 yields 310 mg of the title compound as an oil.

IR: 3600, 3400, 2952, 2860, 1712, 978 cm$^{-1}$.

EXAMPLE 17

(5Z,13E)-(9S,11R,15R)-9-Chloro-11,15-dihydroxy-16-phenoxy-17,18,19,20-tetranor-5,13-prostadienoic Acid Methyl Ester A solution of 910 mg of (5Z,13E)-(9R,11R,15R)-9-hydroxy-11,15-bis(tetrahydropyran-2-yloxy)-16-phenoxy-17,18,19,20-tetranorprostadienoic acid methyl ester, 560 mg of triphenylphosphine, and 260 mg of carbon tetrachloride in 5 ml of acetonitrile is heated for 2 hours to 80° C. For working up purposes, the mixture is diluted with 100 ml of water, extracted three times with respectively 50 ml of n-heptane, the organic extract is washed with brine, dried over magnesium sulfate, and evaporated under vacuum. The residue is chromatographed on silica gel with hexane/ether (2+1), thus obtaining 510 mg of the 9o-chloro compound as an oil.

IR: 2955, 2870, 1735, 1600, 1590, 1100, 980 cm$^{-1}$.

To split off the blocking groups, the compound is treated with the acetic acid mixture corresponding to Example 1, thus obtaining 300 mg of the title compound as an oil. IR: 3600, 3400, 2950, 1735, 1601, 1590, 976 cm$^{-1}$.

The methyl ester of (5Z,13E)-(9R,11R,15R)-9-hydroxy-11,15-bis(tetrahydropyran-2-yloxy)-16-phenoxy-17,18,19,20-tetranorprostadienoic acid used as the starting material is prepared as follows:

A solution of 3 g of the 9-tosylate obtained according to Example 1 in 100 ml of dimethyl sulfoxide is heated with 6 g of potassium nitrite for 3 hours to 60° C. After cooling the mixture is diluted with 800 ml of water, extracted three times with respectively 100 ml of hexane/ether (2+1), the combined extracts are washed twice with respectively 20 ml of brine, dried over magnesium sulfate, and evaporated under vacuum. The residue is purified on silica gel with hexane and increasing ethyl acetate gradients. Yield: 1.5 g of (9R)-9β-hydroxy compound as an oil.

EXAMPLE 18

(5Z,13E)-(9S,11R,15R)-9-Chloro-11,15-dihydroxy-16-phenoxy-17,18,19,20-tetranor-5,13-prostadienoic Acid Analogously to Example 2, 250 mg of the compound prepared according to Example 17 yields 190 mg of the title compound as an oil.

IR: 3600, 3410, 2960, 2870, 1710, 1600, 1588, 978 cm$^{-1}$.

EXAMPLE 19

(5Z,13E)-(9R,11R,15R)-9-Chloro-11,15-dihydroxy-16-phenoxy-17,18,19,20-tetranor-5,13-prostadienoic Acid Methylsulfonamide A solution of 200 mg of (5Z,13E)-(9R,11R,15R)-9-chloro-11,15-dihydroxy-16-phenoxy-17,18,19,20-tetranor-5,13-prostadienoic acid in 5 ml of dimethylformamide is combined at 0° C. with 80 mg of the butyl ester of chloroformic acid and 60 mg of triethylamine. After 30 minutes, 234 mg of the sodium salt of methylsulfonamide (prepared from methylsulfonamide and sodium methylate) and 2 ml of hexamethylphosphoric triamide are added, and the mixture is stirred for 3 hours at 20° C. Subsequently, the reaction mixture is poured on a citrate buffer (pH 5), extracted repeatedly with ethyl acetate, the organic phase washed with brine, dried over magnesium sulfate, and evaporated under vacuum. After chromatography of the residue on silica gel with methylene chloride, 80 mg of the title compound is obtained as an oil.

IR: 3600, 3400, 1718, 1600, 1590, 1125, 972 cm$^{-1}$.

EXAMPLE 20

(13E)-(9R,11R,15R)-9-Chloro-11,15-dihydroxy-16-phenoxy-17,18,19,20-tetranor-5,13-prostadienoic Acid Methylsulfonamide Analogously to Example 19, the compound prepared according to Example 4 yields the title compound in the form of an oil.

IR: 3605, 3410, 1720, 1600, 1588, 1125, 970 cm$^{-1}$.

EXAMPLE 21

(5Z,13E)-(9R,11R,15R)-9-Chloro-11,15-dihydroxy-16-(m-chlorophenoxy)-17,18,19,20-tetranor-5,13-prostadienoic Acid Methylsulfonamide Analogously to Example 19, the compound produced by following Example 6 yields the title compound as an oil.

IR: 3602, 3400, 1720, 1602, 1590, 1130, 970 cm$^{-1}$.

EXAMPLE 22

(13E)-(9R,11R,15R)-9-Chloro-11,15-dihydroxy-16-(m-chlorophenoxy)-17,18,19,20-tetranor-13-prostenoic Acid Methylsulfonamide In analogy to Example 19, the compound prepared according to Example 8 produces the title compound in the form of an oil.

IR: 3602, 3400, 2960, 2870, 1720, 1601, 1590, 1125, 970 cm$^{-1}$.

EXAMPLE 23

(5Z,13E)-(9R,11R,15R)-9-Chloro-11,15-dihydroxy-16,16-dimethyl-5,13-prostadienoic Acid Methylsulfonamide A solution of 585 mg of (5Z,13E)-(9R,11R,15R)-9-chloro-16,16-dimethyl-11,15-bis(tetrahydropyran-2-yloxy)-5,13-prostadienoic acid (obtained from the methyl ester—see Example 9—by saponification with 1-molar sodium hydroxide solution in methanol) in 25 ml of tetrahydrofuran is combined with 0.75 mg of methanesulfonyl isocyanate in 10 ml of tetrahydrofuran and agitated for 6 hours at 20° C. The mixture is then neutralized with acetic acid, concentrated under vacuum, the residue is dissolved in 100 ml of methylene chloride, shaken with saturated sodium bicarbonate solution and with water, dried over magnesium sulfate, and evaporated under vacuum.

To split off the blocking groups, the residue is stirred for 4 hours at 40° C. with 10 ml of a mixture of glacial acetic acid/water/tetrahydrofuran (65+35+10), evaporated under vacuum, and the residue absorbed on 20 g of silica gel. By elution with hexane/ethyl acetate (1+1), impurities are separated. With ethyl acetate, 200 mg of the title compound is then eluted in the form of an oil.

IR: 3600, 3420, 2955, 2868, 1718, 112.0, 972 cm$^{-1}$.

EXAMPLE 24

(5Z,13E)-(9R,11R,16RS)-9-Chloro-11,15α-dihydroxy-16-methyl-5,13-prostadienoic Acid Methylsulfonamide Analogously to Example 19, the compound prepared according to Example 12 yields the title compound as an oil.

IR: 3602, 3400, 1718, 1120, 972 cm$^{-1}$.

EXAMPLE 25

(5Z,13E)-(9R,11R,15R)-9-Chloro-11,15-dihydroxy-16-phenoxy-17,18,19,20-tetranor-5,13-prostadienoic Acid Isopropylsulfonamide 200 mg of (5Z,13E)-(9R,11R,15R)-9-chloro-11,15-dihydroxy-16-phenoxy-17,18,19,20-tetranor-5,13-prostadienoic acid (from Example 2) is dissolved in 5 ml of dimethylformamide and combined at 0° C. with 80 mg of the isobutyl ester of chloroformic acid and 60 mg of triethylamine. After 30 minutes, 290 mg of the sodium salt of isopropylsulfonamide (prepared from isopropylsulfonamide and sodium methylate) and 2 ml of hexamethylphosphoric triamide are added thereto, and the mixture is stirred for 3 hours at 25° C. To work up the mixture, it is poured on 100 ml of citrate buffer (pH 5), extracted repeatedly with ethyl acetate, the organic phase washed with brine, dried over magnesium sulfate, and evaporated under vacuum. After chromatography of the residue on silica gel with methylene chloride, 91 mg of the title compound is obtained as an oil.

IR: 3600, 3410, 2960, 2870, 1722, 1601, 1588, 1120, 974 cm$^{-1}$.

EXAMPLE 26

(13E)-(9R,11R,15R)-9-Chloro-11,15-dihydroxy-16-phenoxy-17,18,19,20-tetranor-13-prosteonic Acid Isopropylsulfonamide In analogy to Example 25, 200 mg of (13E)-(9R,11R,15R)-9-chloro-11,15-dihydroxy-16-phenoxy-17,18,19,20-tetranor-13-prostenoic acid (preparation see Example 4) yields 85 mg of the title compound as an oil.

IR: 3605, 3410, 2955, 2865, 1722, 1600, 1588, 1125, 974 cm$^{-1}$.

EXAMPLE 27

(5Z,13E)-(9R,11R,15R)-9-Chloro-11,15-dihydroxy-16-phenoxy-17,18,19,20-tetranor-5,13-prostadienoic Acid Acetylamide At 25° C., 150 mg of triethylamine is added to a solution of 575 mg of (5Z,13E)-(9R,11R,15R)-9-chloro-11,15-bis(tetrahydropyran-2-yloxy)-16-phenoxy-17,18,19,20-tetranor-5,13-prostadienoic acid (prepared from the corresponding methyl ester—see Example 1—by saponification with 1-molar sodium hydroxide solution in methanol) in 15 ml of acetonitrile; the mixture is cooled to 0° C., and a solution of 106 mg of acetyl isocyanate in 10 ml of acetonitrile is added dropwise. Thereafter the mixture is stirred for 2 hours at 25° C., concentrated under vacuum, diluted with 100 ml of water, adjusted to pH 5 by adding 1N sulfuric acid, extracted repeatedly with ether, and the organic phase washed with brine, dried over magnesium sulfate, and evaporated under vacuum. To split off the blocking group, the residue is stirred for 5 hours at 40° C. with 15 ml of glacial acetic acid/water/tetrahydrofuran (65+35+10) and then evaporated to dryness under vacuum. The residue is chromatographed on silica gel with methylene chloride/1% isopropyl alcohol, thus obtaining 220 mg of the title compound as an oil.

IR: 3600, 3400, 2945, 2862, 1708, 1600, 1588, 976 cm$^{-1}$.

EXAMPLE 28

(13E)-(9R,11R,15R)-9-Chloro-11,15-dihydroxy-16-phenoxy-17,18,19,20-tetranor-13-prostenoic Acid Acetylamide Analogously to Example 27, 450 mg of (13E)-(9R,11R,15R)-9-chloro-11,15-bis(tetrahydroyran-2-yloxy)-16-phenoxy-17,18,19,20-tetranor-13-prostenoic acid (prepared from the corresponding methyl ester— see Example 3—by saponification with 1-molar sodium hydroxide solution in methanol) yields 200 mg of the title compound as an oil.

IR: 3600, 3410, 2950, 2860, 1706, 1600, 1590, 976 cm$^{-1}$.

EXAMPLE 29

(13E)-(9R,11R,15R)-9-Chloro-11,15-dihydroxy-16-(m-chlorophenoxy)-17,18,19,20-tetranor-13-prostenoic Acid Acetylamide In analogy to Example 27, 485 mg of (13E)-(9R,11R,15R)-9-chloro-11,15-bis(tetrahydropyran-2-yloxy)-16-(m-chlorophenoxy)-17,18,19,20-tetranor-13-prostenoic acid (prepared from the corresponding methyl ester—see Example 7—by saponification with 1-molar sodium hydroxide solution in methanol) yields 225 mg of the title compound as an oil.

IR: 3600, 3400, 2948, 2858, 1706, 1602, 1590, 976 cm$^{-1}$.

EXAMPLE 30

(5Z,13E)-(9R,11R,15R)-9-Chloro-11,15-dihydroxy-16-phenoxy-17,18,19,20-tetranor-5,13-prostadienoic Acid Amide 400 mg of (5Z,13E)-(9R,11R,15R)-9-chloro-11,15-dihydroxy-16-phenoxy-17,18,19,20-tetranor-5,13-prostadienoic acid (preparation see Example 2) is dissolved in 10 ml of tetrahydrofuran and combined at 0° C. with 140 mg of triethylamine and 171 mg of the isobutyl ester of chloroformic acid. After 1 hour, gaseous ammonia is introduced at 0° C. for 10 minutes, and then the mixture is allowed to stand for 1 hour at 25° C. Subsequently, the mixture is diluted with 50 ml of water, extracted three times with respectively 50 ml of methylene chloride, the combined extracts are shaken once with 20 ml of brine, dried over magnesium sulfate, and evaporated under vacuum. For purifying purposes, the residue is chromatographed on silica gel with chloroform/ethyl acetate mixtures, thus obtaining 310 mg of the title compound as a waxy mass.

IR: 3600, 3535, 3415, 2995, 2930, 2860, 1675, 1600, 1588, 972 cm$^{-1}$.

EXAMPLE 31

(13E)-(9R,11R,15R)-9-Chloro-11,15-dihydroxy-16-phenoxy-17,18,19,20-tetranor-13-prosteonic Acid Amide Analogously to Example 30, the title compound in the form of an oil is obtained from the acid prepared according to Example 4.

IR: 3600, 3535, 3410, 2996, 2930, 2860, 1670, 1601, 1588, 972 cm$^{-1}$.

EXAMPLE 32

(5Z,13E)-(9R,11R,15R)-9-Chloro-11,15-dihydroxy-16-(m-chlorophenoxy)-17,18,19,20-tetranor-5,13-prostadienoic Acid Amide In analogy to Example 30, the acid prepared according to Example 6 yields the title compound in the form of an oil.

IR: 3600, 3450, 2998, 2930, 2862, 1670, 1600, 1585, 974 cm$^{-1}$.

EXAMPLE 33

(13E)-(9R,11R,15R)-9-Chloro-11,15-dihydroxy-16-(m-chlorophenoxy)-17,18,19,20-tetranor-13-prostenoic Acid Amide Analogously to Example 30, the acid produced according to Example 8 yields the title compound as an oil.

IR: 3600, 3420, 2998, 2935, 2860, 1672, 1600, 1588, 972 cm$^{-1}$.

EXAMPLE 34

(13E)-(9R,11R,15R)-9-Chloro-11,15-dihydroxy-16-phenoxy-17,18,19,20-tetranor-13-prostenoic Acid Tris(hydroxymethyl)aminomethane Salt At 65° C., a solution of 122 mg of tris(hydroxymethyl)aminomethane in 0.4 ml of water is added to a solution of 410 mg of (13E)-(9R,11R,15R)-9-chloro-11,15-dihydroxy-16-phenoxy-17,18,19,20-tetranor-13-prostenoic acid (preparation see Example 4) in 70 ml of acetonitrile. The mixture is allowed to cool down under stirring, decanted from the solvent after 16 hours, and the residue dried under vacuum, thus obtaining 365 mg of the title compound as a white, waxy mass.

EXAMPLE 35

(5Z,13E)-(8R,9R,11R,12R,15S,16RS)-9-Chloro-11,15-dihydroxy-16,19-dimethyl-5,13,18-prostatrienoic Acid Under argon, 915 mg of (5Z,13E)-(8R,9R,11R,12R,15S,16RS)-9-chloro-11,15-bis(tetrahydropyran-2-yloxy)-16,19-dimethyl-5,13,18-prostatrienoic acid was stirred at room temperature for 17 hours with 19 ml of a mixture of acetic acid/water/tetrahydrofuran (65/35/10). The mixture was evaporated thereafter under vacuum and the residue purified by column chromatography on silanized silica gel with ethanol/water (1:1), thus obtaining 94 mg of the title compound.

IR (Film): 3370 (broad), 1710 cm$^{-1}$.

The starting material for the above title compound was produced as follows:

(35a)
(5Z,13E)-(8R,9R,11R,12R,15S,16RS)-9-Chloro-11,15-bis(tetrahydropyran-2-yloxy)-16,19-dimethyl-5,13,18-prostatrienoic Acid Methyl Ester A solution of 1.09 g of (5Z,13E)-(8R,9S,11R,12R,15S,16RS)-9-hydroxy-11,15-bis(tetrahydropyran-2-yloxy)-16,19-dimethyl-5,13,18-prostatrienoic acid methyl ester, 760 mg of triphenylphosphine, and 14.5 ml of a solution of 0.97 ml of carbon tetrachloride, 0.79 ml of pyridine, and 48 ml of acetonitrile were agitated under argon at room temperature for 69 hours. The mixture was then diluted with 15 ml of ether and 30 ml of hexane, further stirred for 10 minutes, and filtered. The residue from the evaporation was extracted with a mixture of 5 ml of ether and 95 ml of hexane, filtered, and evaporated to dryness under vacuum. The residue was purified by column chromatography on silica gel with hexane/20–33% ethyl acetate as the eluent, thus isolating 1.04 g of the desired compound.

IR (Film): 1740, 1132, 1080, 1035, 1025, 975 cm$^{-1}$.

(35b)
(5Z,13E)-(8R,9R,11R,12R,15S,16RS)-9-Chloro-11,15-bis(tetrahydropyran-2-yloxy)-16,19-dimethyl-5,13,18-prostatrienoic Acid 942 mg of the ester obtained according to the above directions was introduced into 16.2 ml of a solution of 3.6 g of potassium hydroxide, 24 ml of water, and 120 ml of methanol, and the mixture was agitated at room temperature for 7.5 hours. The reaction mixture was then diluted with water, washed with ether, and subsequently acidified at about 5° C. to pH 5 with 10% citric acid solution. The mixture was then extracted five times with methylene chloride, the combined organic extracts were washed with saturated sodium chloride solution, dried over magnesium sulfate, and concentrated under vacuum. The residue from the evaporation (915 mg) could be utilized without further purification in the subsequent reaction stage.

EXAMPLE 36
(5Z,13E)-(8R,9S,11R,12R,15S,16RS)-9-Chloro-11,15-dihydroxy-16,19-dimethyl-5,13,18-prostatrienoic Acid A solution of 144 mg of (5Z,13E)-(8R,9S,11R,12R,15S,16RS)-9-chloro-11,15-bis(tetrahydropyran-2-yloxy)-16,19-dimethyl-5,13,18-prostatrienoic acid in 2 ml of absolute ethanol was combined with 6.4 mg of pyridine p-toluenesulfonate and agitated for 5 days at room temperature under argon. The reaction mixture was then diluted with 100 ml of methylene chloride, washed twice with saturated sodium chloride solution, dried over magnesium sulfate, and evaporated to dryness under vacuum. The residue was purified by column chromatography on silica gel with hexane/50–100% ethyl acetate as the eluent, thus obtaining 42.5 mg of the desired carboxylic acid as a highly viscous oil.

IR (Film): 3390 (broad), 1710 cm$^{-1}$.

The starting material for the above title compound was produced as follows:

(36a)
(5Z,13E)-(8R,11R,12R,15S,16RS)-9-Oxo-11,15-bis(tetrahydropyran-2-yloxy)-16,19-dimethyl-5,13,18-prostatrienoic Acid Methyl Ester A solution of 1.23 g of (5Z,13E)-(8R,9S,11R,12R,15S,16RS)-9-hydroxy-11,15-bis(tetrahydropyran-2-yloxy)-16,19-dimethyl-5,13,18-prostatrienoic acid methyl ester in 20 ml of absolute acetone was combined at −20° C. with 1.54 ml of Jones reagent. The mixture was allowed to rest at this temperature for 45 minutes, then combined dropwise with 2 ml of isopropanol, stirred for 10 minutes, diluted with ether, and washed three times with saturated sodium chloride solution. The organic phase was dried over magnesium sulfate and concentrated to dryness under vacuum. The residue was utilized in the subsequent reaction stage without further purification, thus isolating 1.16 g of ketone.

(36b)
(5Z,13E)-(8R,9R,11R,12R,15S,16RS)-9-Hydroxy-11,15-bis(tetrahydropyran-2-yloxy)-16,19-dimethyl-5,13,18-prostatrienoic Acid Methyl Ester A solution of 1.16 g of the ketone obtained in the preceding reaction stage in 25 ml of absolute methanol was combined at 0° C. with 0.5 g (13 millimoles) of sodium borohydride and left for 25 minutes at this temperature while agitating under an argon atmosphere. The solvent was then removed under vacuum, the residue was combined with 20 ml of water and extracted three times with respectively 100 ml of ether. The combined organic phases were washed neutral with water, dried over magnesium sulfate, and evaporated with a forced circulation evaporator. The residue was purified by column chromatography on silica gel with hexane/50–66% ethyl acetate as the eluent. Following the less polar 9α-alcohol, the desired 9β-title compound was obtained (163 mg).

(36c)
(5Z,13E)-(8R,9S,11R,12R,15S,16RS)-9-Chloro-11,15-bis(tetrahydropyran-2-yloxy)-16,19-dimethyl-5,13,18-prostatrienoic Acid Methyl Ester The 163 mg of 9β-alcohol obtained in the preceding reaction stage was agitated under argon for 19 hours at room temperature together with 114 mg of triphenylphosphine and 2.17 ml of a solution of 0.97 ml of carbon tetrachloride, 0.79 ml of pyridine, and 48 ml of acetonitrile. The mixture was then diluted with ether/hexane, further stirred for 10 minutes, and filtered. After concentration under vacuum, the residue was extracted with a mixture of 5 ml of ether and 95 ml of hexane, filtered, and the solvent therein was removed by means of a forced circulation evaporator. The residue was purified by column chromatography on silica gel with hexane/20% ethyl acetate as the eluent, thus obtaining 159 mg of the title compound.

(36d)
(5Z,13E)-(8R,9S,11R,12R,15S,16RS)-9-Chloro-11,15-bis(tetrahydropyran-2-yloxy)-16,19-dimethyl-5,13,18-prostatrienoic Acid 159 mg (0.27 mmol) of the ester obtained as described above was introduced into 2.8 ml of a solution of 3.6 g of potassium hydroxide, 24 ml of water, and 120 ml of methanol and agitated for 6 hours at room temperature. The reaction mixture was then diluted with water, extracted with ether, and subsequently acidified to pH 5 with 10% citric acid solution at 5° C. The mixture was then extracted five times with methylene chloride, the organic extracts were washed with saturated sodium chloride solution, dried over magnesium sulfate, and concentrated by a forced circulation evaporator. The residue was purified by column chromatography on silica gel with hexane/ethyl acetate (1:1), thus isolating 144 mg.

EXAMPLE 37

(13E)-(8R,9R,11R,12R,15S,16RS)-9-Chloro-11,15-dihydroxy-16,19-dimethyl-13,18-prostadienoic Acid 101 mg of (13E)-(8R,9R,11R,12R,15S,16RS)-9-chloro-11,15-bis(tetrahydropyran-2-yloxy)-16,19-dimethyl-13,18-prostadienoic acid was stirred under argon at room temperature for 25 hours with 2 ml of a mixture of acetic acid/water/tetrahydrofuran (65/35/10). The mixture was then concentrated under vacuum and the residue purified by column chromatography on silica gel with hexane/0–100% ethyl acetate as the eluent, thus producing 31 mg of the desired carboxylic acid.

IR (Film): 3380 (broad), 2730, 2660, 1710 cm$^{-1}$.

The starting material for the above title compound was produced as follows:

(37a)
(13E)-(8R,9S,11R,12R,15S,16RS)-9-hydroxy-16,19-dimethyl-11,15-bis(tetrahydropyran-2-yloxy)-13,18-prostadienoic Acid Methyl Ester A solution of 1.55 g of (13E)-(8R,9S,11R,12R,5S,16RS)-9-hydroxy-16,19-dimethyl-11,15-bis(tetrahydropyran-2-yloxy)-13,18-prostadienoic acid in methylene chloride was treated with ethereal diazomethane solution until the evolution of nitrogen ceased and the solution assumed a permanent yellow color. After removal of excess diazomethane as well as the solvent, the residue (1.58 g) was used without further purification in the subsequent reaction stage.

(37b)
(13E)-(8R,9R,11R,12R,15S,16RS)-9-Chloro-11,15-bis(tetrahydropyran-2-yloxy)-16,19-dimethyl-13,18-prostadienoic Acid Methyl Ester A solution of 804 mg of the ester obtained as described above in 10.7 ml of a solution of 0.97 ml of carbon tetrachloride, 0.79 ml of pyridine, and 48 ml of acetonitrile was stirred under argon for 73 hours at room temperature with 560 mg of triphenylphosphine. Thereafter the mixture was diluted with 16 ml of ether and 32 ml of hexane, further agitated for 10 minutes, filtered, and concentrated by means of a forced circulation evaporator. The residue from the evaporation was extracted with a mixture of 5 ml of ether and 95 ml of hexane, filtered, and concentrated to dryness under vacuum. The residue was purified by column chromatography on silica gel with methylene chloride/20% ethyl acetate as the eluent, thus obtaining 225.7 mg of the title compound.

(37c)
(13E)-(8R,9R,11R,12R,15S,16RS)-9-Chloro-11,15-bis(tetrahydropyran-2-yloxy)-16,19-dimethyl-13,18-prostadienoic Acid The 225.7 mg of ester obtained in the preceding reaction stage was introduced into 3.9 ml of a solution of 3.6 g of potassium hydroxide, 2.4 ml of water, and 120 ml of methanol and agitated for 6.5 hours at room temperature. The reaction mixture was then diluted with water, extracted with ether, and then acidified to pH 5 at 50° C. with 10% citric acid solution. Thereafter the mixture was extracted five times with methylene chloride, the combined organic extracts were washed with saturated sodium chloride solution, dried over magnesium sulfate, and concentrated by a forced circulation evaporator. The residue (212.5 mg) was utilized in the subsequent stage without further purification.

EXAMPLE 38

(13E)-(8R,9R,11R,12R,15S,16RS)-9-Chloro-11,15-dihydroxy-16,19-dimethyl-13,18-prostadienoic Acid Methylsulfonylamide 103 mg of (13E)-(8R,9R,11R,12R,15S,16RS)-9-chloro-11,15-bis(tetrahydropyran-2-yloxy)-16,19-dimethyl-13,18-prostadienoic acid methylsulfonylamide was stirred for 24.5 hours under argon at room temperature with 1.9 ml of a mixture of acetic acid/water/tetrahydrofuran (65/35/10). Then the mixture was concentrated under vacuum and the residue purified by column chromatography on silica gel with hexane/0–100% ethyl acetate as the eluent, thus obtaining 34.3 mg of the title compound.

The starting material for the above compound was obtained as follows:

(38a)
(13E)-(8R,9R,11R,12R,15S,16RS)-9-Chloro-11,15-bis(tetrahydropyran-2-yloxy)-16,19-dimethyl-13,18-prostadienoic Acid Methylsulfonylamide 111 mg of the carboxylic acid obtained according to Example (37c) was dissolved in 2.5 ml of absolute acetonitrile and combined under argon with 0.04 ml of triethylamine. After cooling to −5° C., the mixture was combined dropwise with a solution of 53 mg of methanesulfonyl isocyanate in 2.5 ml of absolute acetonitrile and thereafter stirred for 2.5 hours at this temperature. The reaction mixture was then concentrated by a forced circulation evaporator, taken up in 1.5 ml of water, acidified to pH 4 with 5% sulfuric acid, and extracted three times with respectively 90 ml of ether. The combined organic phases were washed neutral with saturated sodium chloride solution, dried over magnesium sulfate, and concentrated to dryness under vacuum. The residue was purified by column chromatography on silica gel with hexane/0–50% ethyl acetate as the eluent, thus obtaining 103 mg of the desired compound.

EXAMPLE 39

(5Z,13E)-(8R,9R,11R,12R,15S,16RS)-9-Chloro-11,15-dihydroxy-16,19-dimethyl-5,13,18-prostatrienoic Acid Methylsulfonylamide 156 mg of (5Z,13E)-(8R,9R,11R,12R,15S,16RS)-9-chloro-11,15-bis(tetrahydropyran-2-yloxy)-16,19-dimethyl-5,13,18-prostatrienoic acid methylsulfonylamide was stirred for 16 hours under argon at room temperature with 3 ml of a mixture of acetic acid/water/tetrahydrofuran (65/35/10). The mixture was then evaporated under vacuum and the residue purified by column chromatography on silica gel with methylene chloride/5–30% isopropanol as the eluent, thus obtaining 62 mg of the desired compound.

IR (Film): 3480, 3360, 3260, 1710, 1340, 1150 cm$^{-1}$.

The starting material for the title compound was produced as follows:

(39a)
(5Z,13E)-(8R,9R,11R,12R,15S,16RS)-9-Chloro-11,15-bis(tetrahydropyran-2-yloxy)-16,19-dimethyl-5,13,18-prostatrienoic Acid Methylsulfonylamide 198 mg of the carboxylic acid produced according to Example (35b) was dissolved in 4.3 ml of absolute acetonitrile and combined under argon with 0.066 ml of triethylamine. After cooling to −5° C., the mixture was combined dropwise with a solution of 95 mg of methanesulfonyl isocyanate in 4.3 ml of absolute acetonitrile and thereafter stirred at this temperature for 2.25 hours. The reaction mixture was then taken up in 2.8 ml of water, acidified to pH 4 with 5% sulfuric acid, and extracted three times with respectively 90 ml of ether. The combined organic phases were washed neutral with saturated sodium chloride solution, dried over magnesium sulfate, and evaporated to dryness under vacuum. The residue was purified by column chromatography on silica gel with methylene chloride/5% isopropanol as the eluent, thus obtaining 156 mg of the title compound.

EXAMPLE 40

(5Z,13E)-(8R,9R,11R,12R,15R)-9-Chloro-11,15-dihydroxy-16,16,19-trimethyl-5,13,18-prostatrienoic Acid 1.04 g of (5Z,13E)-(8R,9R,11R,12R,15R)-9-chloro-11,15-bis(tetrahydropyran-2-yloxy)-16,16,19-trimethyl-5,13,18-prostatrienoic acid was stirred under argon at room temperature for 19 hours with 21 ml of a mixture of acetic acid/water/tetrahydrofuran (65/35/10). The mixture was then evaporated under vacuum and the residue purified by column chromatography on silica gel with hexane/0-100% ethyl acetate as the eluent, thus obtaining 380 mg of the title compound.

IR (Film): 3360 (broad), 1710 cm$^{-1}$.

The starting material for the above compound was produced as follows:

(40a)
(5Z,13E)-(8R,9R,11R,12R,15R)-9-Chloro-11,15-bis(tetrahydropyran-2-yloxy)-16,16,19-trimethyl-5,13,18-prostatrienoic Acid Methyl Ester A solution of 1.15 g of (5Z,13E)-(8R,9S,11R,12R,15R)-9-hydroxy-11,15-bis(tetrahydropyran-2-yloxy)-16,16,19-trimethyl-5,13,18-prostatrienoic acid methyl ester, 780 mg of triphenylphosphine, and 15 ml of a solution of 0.97 ml of carbon tetrachloride, 0.79 ml of pyridine, and 48 ml of acetonitrile was stirred for 55 hours under argon at room temperature. The mixture was then diluted with 15 ml of ether and 30 ml of hexane, further stirred for 10 minutes, and filtered. The residue from the evaporation was extracted with a mixture of 5 ml of ether and 95 ml of hexane, filtered, and concentrated to dryness under vacuum. The residue was purified by column chromatography on silica gel with hexane/20-50% ethyl acetate as the eluent, thus obtaining 1.07 g of the desired compound.

IR (Film): 1740, 1130, 1075, 1035, 1025, 70 cm$^{-1}$.

(40b)
(5Z,13E)-(8R,9R,11R,12R,15R)-9-Chloro-11,15-bis(tetrahydropyran-2-yloxy)-16,16,19-trimethyl-5,13,18-prostatrienoic Acid 1.07 g of the ester obtained according to the above description was introduced into 18 ml of a solution of 3.6 g of potassium hydroxide, 24 ml of water, and 120 ml of methanol and stirred at room temperature for 8 hours. The reaction mixture was then diluted with water, washed with ether, and subsequently acidified to pH 5 at about 5° C. with 10% citric acid solution. The mixture is thereafter extracted five times with methylene chloride, the combined organic extracts were washed with saturated sodium chloride solution, dried over magnesium sulfate, and concentrated under vacuum. The residue from the evaporation (1.04 g) could be utilized without further purification in the subsequent reaction stage.

EXAMPLE 41

(5Z,13E)-(8R,9R,11R,12R,15R)-9-Chloro-11,15-dihydroxy-16,16,19-trimethyl-5,13,18-prostatrienoic Acid Methyl Ester 100 mg of the carboxylic acid obtained according to Example 40 was dissolved in methylene chloride and combined with such a quantity of ethereal diazomethane solution that the nitrogen evolution ceased and the yellow color of the solution became permanent. After evaporation of the excess diazomethane and of the solvent under vacuum at room temperature, 101 mg of the desired ester was obtained.

IR (Film): 3400 (broad), 1735 cm$^{-1}$.

EXAMPLE 42

(13E)-(8R,9R,11R,12R,15S)-9-Chloro-11,15-dihydroxy-19-methyl-13,18-prostadienoic Acid Acetylamide 460 mg of (13E)-(8R,9R,11R,12R,15R)-9-chloro-11,15-bis(tetrahydropyran-2-yloxy)-19-methyl-13,18-prostadienoic acid acetylamide was stirred under argon at room temperature for 17 hours with 10 ml of a mixture of acetic acid/water/tetrahydrofuran (65/35/10). The mixture was then concentrated under vacuum, and the residue was purified by column chromatography on silica gel with hexane/0-100% ethyl acetate as the eluent, thus obtaining 197 mg of the title compound.

IR (Film) 3400, 1703 cm$^{-1}$.

The starting material for the above compound was prepared as follows:

(42a)
(13E)-(8R,9R,11R,12R,15S)-9-Chloro-19-methyl-11,15-bis(tetrahydropyran-2-yloxy)-13,18-prostadienoic Acid Methyl Ester A solution of 1.0 g of (13E)-(8R,9S,11R,12R,15S)-9-hydroxy-19-methyl-11,15-bis(tetrahydropyran-2-yloxy)-13,18-prostadienoic acid methyl ester in 14 ml of a solution of 0.97 ml of carbon tetrachloride, 0.79 ml of pyridine, and 48 ml of acetonitrile was stirred together with 730 mg of triphenylphosphine for 70 hours at room temperature under argon. Thereafter the mixture was diluted with 16 ml of ether and 32 ml of hexane, further agitated for 10 minutes, filtered, and concentrated by means of a forced circulation evaporator. The evaporation residue was extracted with a mixture of 5 ml of ether and 95 ml of hexane, filtered, and concentrated to dryness under vacuum. The residue was purified by column chromatography on silica gel with hexane/20% ethyl acetate as the eluent, thus obtaining 720 mg of the title compound.

(42b)
(13E)-(8R,9R,11R,12R,15S)-9-Chloro-11,15-bis(tetrahydropyran-2-yloxy)-19-methyl-13,18-prostadienoic Acid The 720 mg of ester produced in the preceding reaction stage was introduced into 13 ml of a solution of 3.6 mg of potassium hydroxide, 2.4 ml of water, and 120 ml of methanol, and agitated for 7 hours at room temperature. The reaction mixture was then diluted with water, extracted with ether, and thereupon acidified to pH 5 at 5° C. with 10% citric acid solution. Then the mixture was extracted five times with methylene chloride, the combined organic extracts were mixed with saturated sodium chloride solution, dried over magnesium sulfate, and concentrated by means of a forced circulation evaporator. The residue (630 mg) was utilized in the subsequent stage without further purification.

(42c)
(13E)-(8R,9R,11R,12R,15S)-9-Chloro-11,15-bis(tetrahydropyran-2-yloxy)-19-methyl-13,18-prostadienoic Acid Acetylamide At 25° C., 170 mg of triethylamine was added to a solution of 630 mg of the acid obtained as described above in 17 ml of acetonitrile; the mixture was cooled to 0° C. and a solution of 120 mg of acetyl isocyanate in 10 ml of acetonitrile was added dropwise thereto. Subsequently the mixture was stirred for 2 hours at 25° C., concentrated under vacuum, diluted with 100 ml of water, adjusted to pH 5 by the addition of N sulfuric acid, and extracted several times with ether. The combined organic phases were washed with saturated sodium chloride solution, dried over magnesium sulfate, and concentrated to dryness under vacuum. The residue (460 mg) was used without further purification in the THP ether splitting step.

EXAMPLE 43
(5z, 13E, 18z) 8R, 9R, 11R,12R,15S,16RS)-9,19-Dichloro-11,15-dihydroxy-16-methyl-5,13,18-prostatrienoic Acid Under argon, 427 mg of (5Z,13E,18Z)-(8R,9R,11R,12R,15S,16RS)-9,19-dichloro-16-methyl-11,15-bis(tetrahydropyran-2-yloxy)-5,13,18-prostatrienoic acid was stirred at room temperature for 16 hours with 9 ml of a mixture of acetic acid/water/tetrahydrofuran (65/35/10). The mixture was then evaporated under vacuum and the residue purified by column chromatography on silica gel with hexane/20-80% ethyl acetate, thus producing 180 mg of the title compound.

IR (Film): 3360 (broad), 1710 cm$^{-1}$.

The starting material for the above title compound was prepared as follows:

(43a)
(5Z,13E,18Z)-(8R,9R,11R,12R,15S,16RS)-9,19-Dichloro-16-methyl-11,15-bis(tetrahydropyran-2-yloxy)-5,13,18-prostatrienoic Acid Methyl Ester A solution of 1.16 g of (5Z,13E,18Z)-(8R,9S,11R,12R,15S,16RS)-9-hydroxy-19-chloro-16-methyl-11,15-bis(tetrahydropyran-2-yloxy)-5,13,18-prostatrienoic acid methyl ester, 785 mg of triphenylphosphine, and 15 ml of a solution of 0.97 ml of carbon tetrachloride, 0.79 ml of pyridine, and 48 ml of acetonitrile was stirred under argon at room temperature for 65 hours. The mixture was then diluted with 15 ml of ether and 30 ml of hexane, further stirred for 10 minutes, and filtered. The evaporation residue was extracted with a mixture of 5 ml of ether and 95 ml of hexane, filtered, and concentrated to dryness under vacuum. The residue was purified by column chromatography on silica gel with hexane/10-50% ethyl acetate as the eluent. In this way, 457 mg of the desired compound was isolated.

(43b)
(5Z,13E,18Z)-(8R,9R,11R,12R,15S,16RS)-9,19-Dichloro-16-methyl-11,15-bis(tetrahydropyran-2-yloxy)-5,13,18-prostatrienoic Acid 457 mg of the ester obtained as described above was introduced into 7.6 ml of a solution of 3.6 g of potassium hydroxide, 24 ml of water, and 120 ml of methanol, and stirred for 6 hours at room temperature. The reaction mixture was then diluted with water, washed with ether, and thereafter acidified to pH 5 at about 5° C. with 10% citric acid solution. Then the mixture was extracted five times with methylene chloride, the combined organic extracts were washed with saturated sodium chloride solution, dried over magnesium sulfate, and concentrated under vacuum. The residue from the evaporation could be utilized in the subsequent reaction stage without further purification. Yield: 427 mg of the title compound.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 9-chloroprostane of the formula

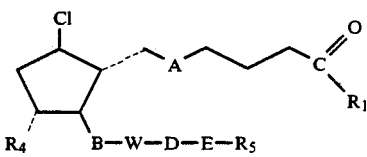

wherein
the 9-chlorine atom can be in the α- or β-position,
$R_1$ or $OR_2$ wherein,
$R_2$ is H; $C_{1-10}$-alkyl; $C_{1-10}$-alkyl substituted by halogen, $C_{1-4}$-alkoxy, $C_{6-10}$-aryl or -aroyl, $C_{6-10}$-aryl or -aroyl substituted by the substituents defined below for the $R_2$ aryl groups, di-$C_{1-4}$-alkylamino, or tri-$C_{1-4}$-alkylammonium; $C_{4-10}$-cycloalkyl; $C_{4-10}$-cycloalkyl substituted by $C_{1-4}$-alkyl; $C_{6-10}$-aryl; $C_{6-10}$-aryl substituted by 1-3 halogen atoms, phenyl, 1-3 $C_{1-4}$-alkyl groups, or a chloromethyl, fluoromethyl, trifluoromethyl, carboxy, hydroxy or $C_{1-4}$-alkoxy group; or an aromatic heterocycle of 5- or 6-total ring atoms and 1-2 hetero N, O or S atoms, the remainder being carbon atoms;
A is cis—CH=CH—,
B is —CH$_2$—CH$_2$—, trans—CH=CH— or —C≡C—,
W is hydroxymethylene or

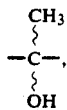

wherein the OH-group in each case can be in the α- or β-position, and can be etherified or esterified by tetrahydropyranyl, tetrahydrofuranyl, α-ethoxyethyl, trimethylsilyl, dimethyl-tert-butylsilyl, tribenzylsilyl, acetyl, propionyl, butyryl or benzoyl;

D and E together represent a direct bond or

D is a straight-chain or branched alkylene group of 1–10 carbon atoms, optionally substituted by fluorine, and E is a direct bond, and $R_4$ is hydroxy or hydroxy etherified or esterified as defined for W above;

$R_5$ is a $C_{1-10}$ hydrocarbon aliphatic group, and

D or $R_5$ is selected such that the 16position of the resultant prostadienoic acid compound is substituted by alkyl or dialkyl, or a physiologically acceptable salt thereof with a base when $R_1$ is OH.

2. A compound of claim 1, wherein D or $R_5$ is selected such that the 16-position of the resultant compound is substituted by alkyl or dialkyl and the 19-position is substituted by alkyl.

3. A compound of claim 1, wherein D or $R_5$ is selected such that the 16-position of the resultant compound is substituted by one or two methyl groups and the 19-position is unsubstituted or is substituted by a methyl group.

4. A compound of claim 1, wherein $R_1$ is OH or $OC_{1-4}$-alkyl.

5. A compound of claim 1, wherein B is a trans—C≡C—.

6. (5Z,13E)-(9R,11R,15R)-9-Chloro-11,15-dihydroxy-16,16-dimethyl-5,13-prostadienoic acid methyl ester, a compound of claim 1.

7. (5Z,13E)-(9R,11R,15R)-9-Chloro-11,15-dihydroxy-16,16-dimethyl-5,13-prostadienoic acid, a compound of claim 1.

8. (5Z,13E)-(9R,11R,16RS)-9-Chloro-11,15α-dihydroxy-16-methyl-5,,13-prostadienoic acid methyl ester, a compound of claim 1.

9. (5Z,13E)-(9R,11R,16RS)-9-Chloro-11,15α-dihydroxy-16-methyl-5,13-prostadienoic acid, a compound of claim 1.

10. A pharmaceutical composition comprising a cytoprotective amount of a compound of claim 1 and a pharmaceutically acceptable carrier.

11. A method of achieving a cytoprotective effect in a patient comprising administering a cytoprotectively effective amount of a compound of claim 7.

12. A method of triggering an abortion in a host in which such treatment is desired comprising administering an amount of a compound of claim 1 effective for such treatment.

13. A method of achieving a cytoprotective effect in a patient comprising administering a cytoprotectively effective amount of a compound of claim 1.

* * * * *